United States Patent [19]

Marlow et al.

[11] Patent Number: 4,911,709
[45] Date of Patent: Mar. 27, 1990

[54] ARTIFICIAL KNEE WITH IMPROVED STABLE LINK-TYPE KNEE JOINT

[75] Inventors: Richard Z. Marlow, Richmond; Denis R. W. May, Esher, both of England

[73] Assignee: J. E. Hanger and Company Limited, London, England

[21] Appl. No.: 236,733

[22] Filed: Aug. 26, 1988

Related U.S. Application Data

[63] Continuation of Ser. No. 38,612, Apr. 15, 1987.

[30] Foreign Application Priority Data

Apr. 16, 1986 [GB] United Kingdom ............... 8609339
Jan. 14, 1987 [GB] United Kingdom ............... 8700780

[51] Int. Cl.$^4$ ............................ A61F 2/80; A61F 2/64
[52] U.S. Cl. ............................ 623/39; 623/43; 623/46
[58] Field of Search .................. 623/27, 33, 39–43, 623/46, 36; 403/408.1, 384

[56] References Cited

U.S. PATENT DOCUMENTS

| | | | |
|---|---|---|---|
| 1,365,205 | 1/1921 | Stinehart | 623/46 X |
| 2,208,275 | 7/1940 | McCann | 623/39 X |
| 3,182,770 | 5/1965 | Shemet | 403/408.1 |
| 3,187,347 | 6/1965 | Terron | 623/43 |
| 3,663,967 | 5/1972 | Vermillion | 623/43 X |
| 3,823,424 | 7/1974 | May | 623/39 |
| 4,023,215 | 5/1977 | Moore | 623/46 X |
| 4,145,766 | 3/1979 | May | 623/39 X |
| 4,310,932 | 1/1982 | Näder et al. | 623/39 |

FOREIGN PATENT DOCUMENTS 358545 1/1962 Switzerland ............... 623/39

Primary Examiner—Richard J. Apley
Assistant Examiner—David J. Bender
Attorney, Agent, or Firm—Shoemaker and Mattare, Ltd.

[57] ABSTRACT

An improved knee prosthesis of the four bar kind employing modified geometry of its links permitting the available degree of flexion to be increased to 143°. A resilient leaf spring provides for extension bias at low angles of flexion, and biases the joint towards its fully flexed position at high angles of flexion. An improved lock for the joint is also provided.

13 Claims, 6 Drawing Sheets

ARTIFICIAL KNEE WITH IMPROVED STABLE LINK-TYPE KNEE JOINT

This is a continuation of application Ser. No. 38,612 filed 4/15/87, now abandoned.

FIELD OF THE INVENTION

This invention concerns improvements in artificial legs, and its object is to provide an improved joint for fitment between a socket for an amputee's upper leg stump and a skin portion of such a leg. A second object is to provide an improved control function for a four-bar knee joint for fitment between a socket for an amputee's upper leg stump and a shin portion of such a leg.

BACKGROUND TO THE INVENTION

We have described in U.S. Pat. No. 3,823,424 a knee mechanism comprising thigh link means for attachment to upper portions of the leg, shin link means for attachment to a shin of the leg, and anterior and posterior link means pivoted between the thigh and shin links, with:

(a) the line joining the pivot between the anterior link means and the shin link means to the pivot between the posterior link means and the shin link means sloping rearwardly and downwardly;

(b) the anterior link means being shorter than the posterior link means;

(c) the pivots on the shin link means spaced apart by more than twice the distance separating the pivots on the thigh link means;

(d) the pivots on the thigh link means disposed at intermediate positions relative to the horizontal positions of the pivots on the shin link means when the leg is in a fully extended position; and (e) the articulation defined by said links having an instantaneous centre of rotation constituted by the intersection point of a line drawn through the pivots of the anterior link means and a line drawn through the pivots of the posterior link means, said centre of rotation being located in substantially the region of that of a natural knee and lying upon a curve that is ascending through approximately 15° of flexion of the knee mechanism from its fully extended position.

The resultant articulated joint provided a stable weight support until it had been flexed through the predetermined angle from the extended position, which was about 15°. The practical joint was capable of flexure to about 120°, to permit a natural sitting posture. To this end both the forward and rearward links were cranked rearwardly from about their mid points to avoid mutual interference. Alteration of the lengths of the links and of their pivot points could be made to adapt the characteristics of the joint to suit the individual stump condition of a patient, but it was found that the angulation between lines intersecting the pivot axes of the links was critical. The particular combination of dimensions found to be important was that the line joining the thigh and shin pivots of the anterior link sloped forwardly and downwardly at an angle of 41° from the vertical and that the included angles in an irregular quadrilateral defined by the pivot positions of the unflexed joint were 146° at the thigh pivot of the anterior link, 49° at the shin pivot of the anterior link, 82° at the thigh pivot of the posterior link and 53° at the shin pivot of the posterior link. The stated angles were found in practice to be absolutely vital. In an experiment, moving the pivot points one at a time by a mere 1/16 inch (equivalent to an average change of included angle of about 0.5°) was found to produce quite unacceptable loss of function. Gaping between the knee part and the front upper edge of the shin part occurred, the maximum degree of flexion was reduced and there was a tendency for angular movement to become locked.

Extensions of the four bar knee idea e.g. to include swing phase control devices are described in our Patent Specification Nos GB-A-1536007 and GB-B-2134392 and for use in wooden knees are described in our Patent Specification GB-A-1546126. The same geometry was illustrated by Robert Kellie & Son in Patent Specification No. 1303738. We have used the four bar knee widely in a range of different devices, but in each instance we have preserved the above geometry because of its critical nature.

A swing phase control mechanism is described in Specification No. GB-A-1536007 and an extension bias mechanism is described in Specification No. GB-B-2134392. A locking mechanism for a mechanism of the four bar knee is described in Specification No. GB-B-2134392.

SUMMARY OF THE INVENTION

In one aspect, this invention is based on the realization that it is possible to increase the degree of flexion to about 140° and even up to 143° in a knee mechanism of the kind described in U.S. Pat. No. 3,823,424 by increasing the length of the rear pivot and positioning the posterior shin pivot appropriately and that this would enable both a natural sitting posture and a posture in which the user squats back on his heels. An operative geometry has the pivots so disposed that when the mechanism is unflexed they define an irregular quadrilateral whose included angles are 157° at the thigh pivot of the anterior link means, 86° at the shin pivot of the anterior link means, 80° at the thigh pivot of the posterior link means and 37° at the shin pivot of the posterior link means.

A second object of the invention is to provide an improved extension bias mechanism for a four-bar knee.

In a second aspect, the invention provides a four bar knee mechanism for an artificial leg comprising thigh link means for attachment to upper portions of the leg, shin link means for attachment to a shin of the leg, and anterior and posterior link means pivoted between the thigh and shin links, wherein the anterior link means moves rearwardly in the latter part of travel of the mechanism from a flexed to an extended state and resilient means acting between the shin link means and the anterior link means biases the anterior link rearwardly to assist extension of the mechanism.

In a first form a coil spring on a support coaxial with a pivot between the anterior link and the shin link has hooked limbs respectively engaging the anterior and shin links. Such a coil spring may have only a limited life and give rise to fretting between the hooked limbs of the spring and the links those limbs engage. In a second and preferred form, therefore, leaf spring means attached to the front of the shin link and upstanding therefrom bears against the anterior link means.

The invention further provides a four bar artificial knee joint having an anterior link that oscillates during movement from a fully flexed to an extended position and resilient means acting between the anterior link and another link of the joint that at low angles of flexion biases the joint towards its extended position and at high angles of flexion biases the joint towards a fully flexed position.

A further object of the invention is to provide a more compact locking mechanism particularly, though not essentially, for use in association with the aforesaid knee mechanism.

Such a locking mechanism comprises a knee joint for an artificial leg comprising a four bar linkage consisting of thigh and shin link means pivotally connected to anterior and posterior link means to define a four bar linkage, in which the anterior link means is cranked so that its thigh end is disposed rearwardly of central portions thereof and carries at its extremity upstanding catch means, and the anterior link means fits and is pivoted between bifurcated brackets depending from the thigh link, which brackets pivotally support posterior facing catch blade means resiliently biased to rotate downwardly, the arrangement being such that the blade travels over and is reverse rotated by the catch means until the unflexed position is reached, when it snap engages an anterior face of the catch means.

In the present knee mechanism the thigh link allows only restricted screwdriver or spanner access to the lower face thereof to permit upper parts of the limb to be fitted. This difficulty is overcome according to a further feature of the invention which provides a four bar artificial knee joint including a thigh link having its top face formed as a flat face with fixing holes grouped in pairs, a posterior group of fixing holes having slots of keyhole formation into which are engageable a first pair of clamping screws or bolts of an upper member of the leg, the upper member being displaced from its final position in which heads of the screws or bolts of the first pair are accessible from the underside of the joint, the member being slid in a posterior direction to its final position and clamping screws or bolts being inserted into an anterior pair of fixing holes.

The use in association with a prosthetic knee joint of an extension buffer formed with a first portion of relatively soft material that serves to absorb kinetic energy as the joint is unflexed and a second portion of relatively hard material for reacting loads is believed to be new.

BRIEF DESCRIPTION OF THE DRAWINGS

Embodiments of the invention will now be described, by way of example only, with reference to the accompanying drawings, in which.

DETAILED DESCRIPTION OF PREFERRED EMBODIMENT

Figure 1:
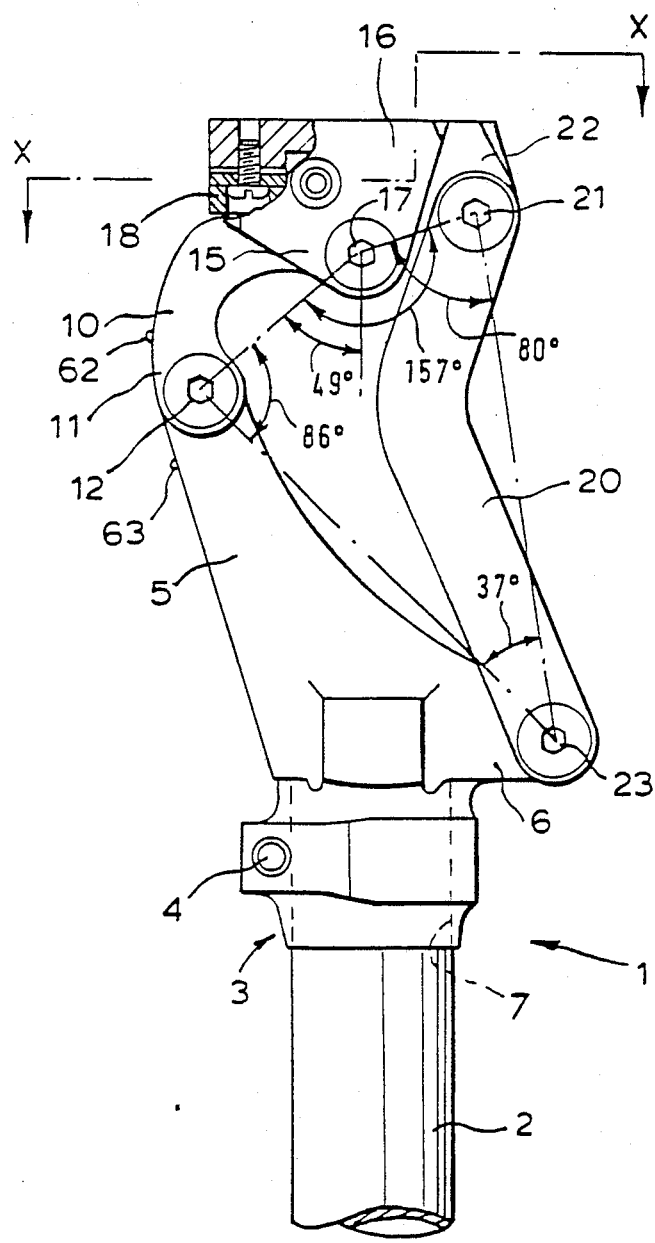
FIG. 1 is an elevation drawn approximately to scale of a knee section of an artificial leg in the extended position.

The shin portion 1 of an artificial leg embodies a tubular load-bearing member 2 attached to a shin link 3 which is conveniently cast or machined from solid as one piece. The tube 2 is retained in a socket 7 at the base of the link 3 by means of a pinch-bolt connector 4. The link 3 has an anterior limb 5 that extends upwardly for an appreciable distance and a posterior limb 6 that extends rearwardly at the same level as the socket so that when link 3 is viewed in side profile it slopes sharply downward towards the rear of the leg. The central region of the anterior limb 5 may be apertured to reduce weight as at 9.

A relatively short anterior link 10 is bifurcated at its lower end 11 to fit either side of the anterior limb 5 to which it is attached by pivot pin 12 and is cranked rearwardly through almost a right-angle to define a body portion 13 formed at the rear edge of the top face with an integral upstanding catch 14. The upper end of the link 10 is fitted between depending bifurcations 15 of a thigh link 16 to which it is secured by pivot pin 17. The thigh link 16 may be connected to a stump socket via an alignment device e.g. as described in our Patent Application No. 8528992 Published under number GB-A-2184160 or as illustrated below with reference to FIGS. 5 and 6.

As shown in GB-A-No. 2184160, a first member of an artificial limb such as a tube socket has a flange 4 formed with through holes grouped into an anterior-posterior pair 5a and a medial lateral pair 5b spaced at 90 degree intervals about the axis of socket 1. The lower face of the flange carries a ball formation 6 of a ball and socket articulation. A second member in the form of angle attachment plate 11 has a concave seat 14 that accepts the ball 6 and threaded bores 17a, 17b conforming to the through holes 5a, 5b. The first and second members are held together by clamping screws 25 received in the bores 17a, 17b that fit onto washers 27 having spherical lower faces that articulate on seats 9. The resulting alignment device is simple to manufacture and preserves angular position when an adjacent pair only of the clamping screws 25 are removed. A similar alignment device having a cylindrical projection articulating in a cylindrical seat under the control of a single pair of clamping screws provides for heel height adjustment.

The anterior edge of the link 16 carries a pad 18 of hard rubber against which the body portion 13 of link 10 abuts to define a fully extended attitude of the knee from which extend primary buffers 18a of somewhat softer rubber. As the knee is unflexed during the swing phase of walking the primary buffers 18a absorb the kinetic energy of the skin and prevent sharp impact between the body portion 13 and the pad 18 but during the stance phase of walking or when the patient is standing, load can be reacted through the pad 18.

A pair of posterior links 20 are pinned at upper pivot 21 to posterior lateral faces 22 of the thigh link 16 and are pivoted at pin 23 to the posterior limb 6 of the shin link 3. It will be noted that the pivots 17, 21 of the thigh link 16 are relatively close together and that a line joining pivot 21 to pivot 17 slopes forwardly and downwardly at a angle of about 15°. The line between pivots 12 and 23 slopes rearwardly and downwardly at an angle of about 45°.

In FIG. 1 the links 3, 10, 16 and 20 form a four-bar kinematic chain with the following characteristics:

(a) the line joining the pivots 12, 23 of the shin link 3 slopes rearwardly and downwardly;

(b) the anterior link 10 is substantialy shorter than the posterior link 20;

(c) the pivots 12, 23 on the shin link 3 are spaced apart by more than twice the distance separating the pivots 17, 21 on the thigh link 16;

(d) the pivots 17, 21 on the thigh link 16 are disposed at intermediate positions relative to the horizontal positions of the pivots 12, 23 on the shin link means 3 when the leg is fully extended;

(e) the instantaneous centre of rotation of the joint defined by the intersection of a line drawn through anterior pivots 17, 12 with a line drawn through posterior pivots 21, 23 is located substantially in the region of that of a natural knee when fitted to a leg and lies upon a curve that is ascending through about 15 degrees of knee flexion from the fully extended position; and (f) the posterior link 23 is of length and has a shin pivot 23 located so that the angulation exhibits flexion exceeding 140° to enable both a natural sitting posture and a posture in which the user squats back on his heels.

It will be noted that in the unflexed position shown in FIG. 1, the pivots 12, 17, 21, 23 form an irregular quadrilateral with respective included angles of 86°, 157°, 80° and 37° and that a line joining pivots 17 and 12 slopes downwardly at an angle of 49° from the vertical.

A further difference between the motion of the knee mechanism of this invention and that of U.S. Pat. No. 3,823,424 is that at high degrees of flexion the pivot 21 joining the posterior link 20 to the thigh link 16 passes to the anterior side of a line joining the pivots 12, 17 of the anterior link, resulting in a distinct "over-centre" action.

Advantageously there is provided a locking mechanism for holding the knee unflexed. For this purpose a blade carrier 30 is pivoted between the bifurcations or cheek plates 15 and has a shaft 31 connected to a handle 32. A coil spring 33 between the body of the link means and the handle 32 biases the carrier 30 so that a rearwardly facing blade 34 on the carrier 30 is biased downwardly. As the joint is unflexed the blade 34 first contacts the top face of the catch 14 by which it is reverse rotated against the resistance of the spring 33. Then as the unflexed positon is reached the blade 34 snaps down against an anterior face of the catch 14, locking the joint unflexed until released via handle 32. The position of the blade 34 may be fixed on the carrier 30 by means of locking screw 35 and gives efficient locking without noticeable play because primary buffers 18a are in compression when the fully unflexed position is reached and the lock is engaged.

Figure 5:
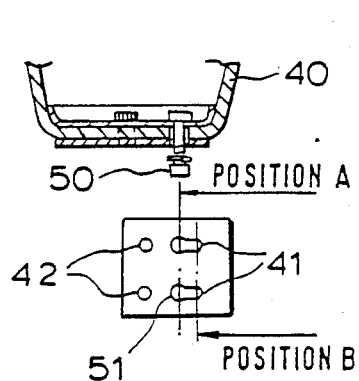
FIG. 5 is a view of a kit for fitting a cup to the top face of a thigh link of the knee section of FIG. 1.
Figure 6:
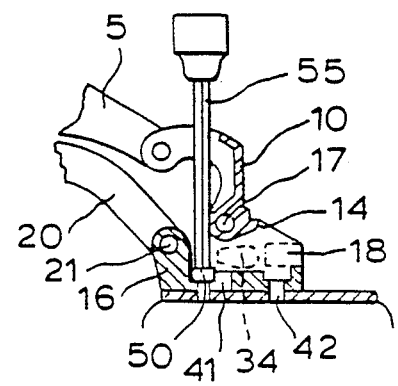
FIG. 6 is a fragmentary side section of the knee mechanism showing the fitting of clamping screws with the knee partly flexed.

In FIGS. 5 and 6 there is shown a fixing kit for attachment of a cup 40 by means of an anterior and posterior pair of fixing screws to a top face of the thigh link 16. A problem with forming such a connection by bolts from the lower face of the thigh link 18 is that locking blade 34 interferes with screwdriver or key access to the posterior pair of fixing holes. Accordingly the cup cooperates with a fixing plate defined by a top face of thigh link 16 having a pair of keyhole posterior apertures 41 and conventional anterior apertures 42. For assembly of the cup 40 to link 16 the buffer pad 18 is removed to give access to the anterior holes 42 in the thigh link 18, posterior cap head screws 50 depending from socket 40 are inserted through the eyes 51 of the keyhole apertures 41 as shown in FIG. 5 in position A, after which the cup 40 is slid in the posterior direction to position B and the knee is partly flexed to the position shown in FIG. 6. The anterior region of keyhole slots 41 is inaccessible from underneath the link 16 because of interference from pivot 17 and blade 34 but the posterior region is accessible from between the front link 10 and the posterior portion of link 16 which provides a bearing for pin 21. Access is given for key 55 to the sockets in cap screws 50 inserted into apertures 41 which are tightened home. Cap screws are inserted into the anterior apertures 42 and tightened home after which primary buffers 18a are inserted from the top face into holes in pad 18 and pad 18 is refitted over the apertures 42. The fitting procedure has been exemplified for a socket cup 40 but other members, e.g. alignment devices, may be fitted in a similar way.

The above knee mechanism lends itself to fitting of a remarkably simple and effective extension bias. In a first form the pivot 12 connecting the lower part of anterior link 10 to the shin link 3 has an extension 60 on which is supported a coil spring 61. The ends of the coil spring 61 are bent to define limbs 62, 63 directed parallel to the axis of the pivot 12 and having hooked ends that engage the anterior portion 5 of link 3 and link 10. The action of the coil spring 61 depends upon angle of flexion because the movement of link 10 during knee flexion is an oscillation rather than a simple rotation. At low angles of flexion the link 10 moves in an anterior direction against the bias of spring 61 which tends to return the knee to its unflexed position. At intermediate angles of flexion the link 10 moves little but at higher degrees of flexion it moves in a posterior direction so that the action of spring 61 is then to assist flexion.

The knee mechanism is used in a cosmesis that resists flexion so that when the user is sitting down his cosmesis tries to straighten the knee again. The opposition by spring 61 to straightening of the knee by the cosmesis means that the finished limb exhibits neutral behavior when flexed to sitting or squatting angles, which is of obvious benefit to the user.

Figure 2:
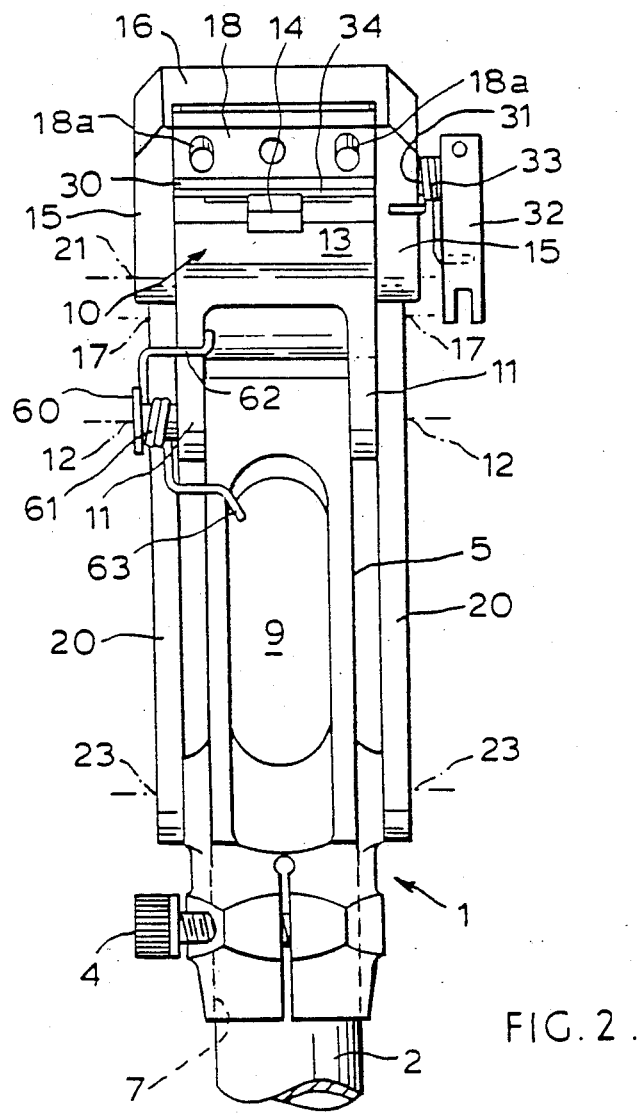
FIG. 2 is a front view of the leg in a partly flexed position.
Figure 3:
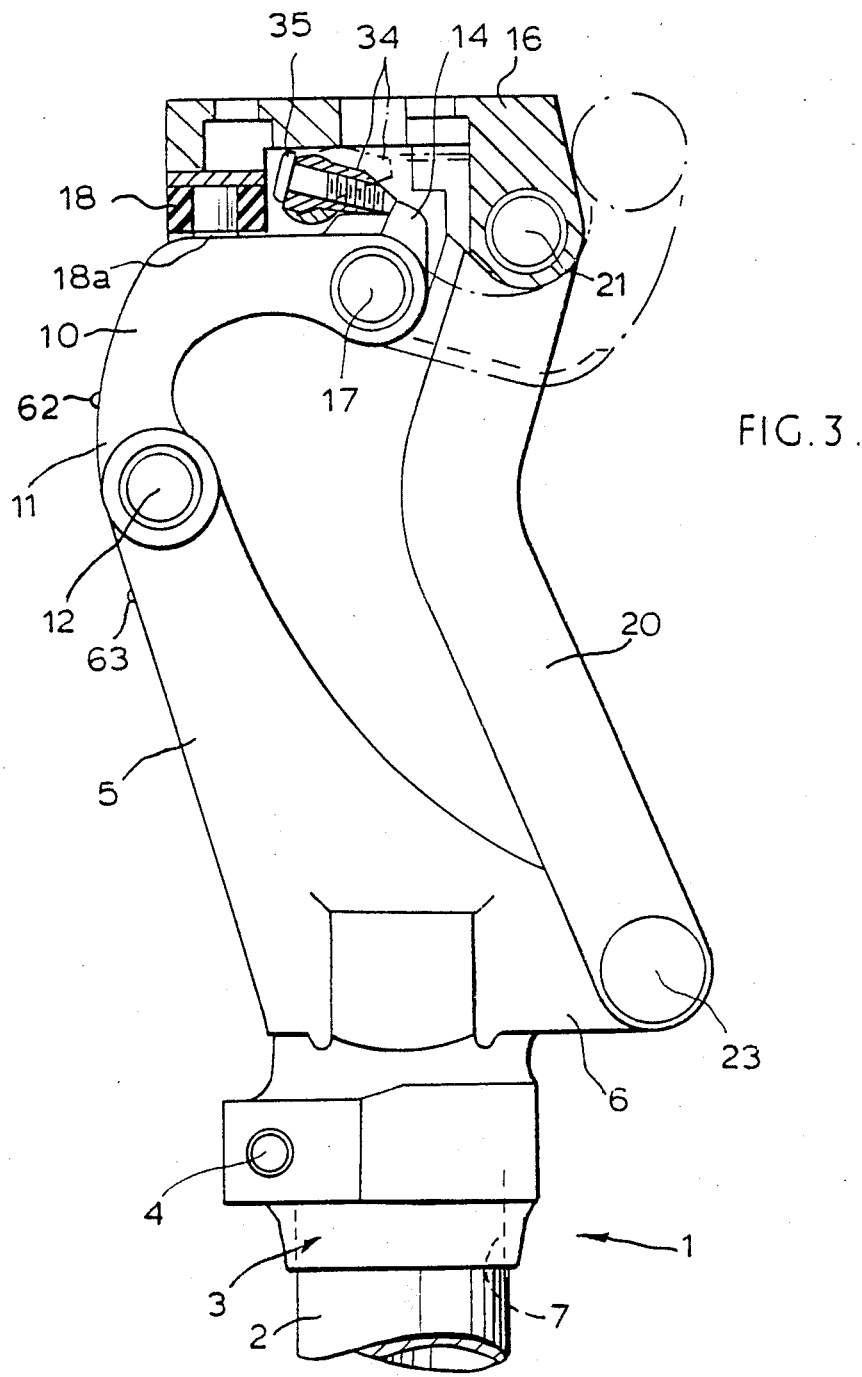
FIG. 3 is a second side elevation of the knee section with the thigh link shown in section.
Figure 4:
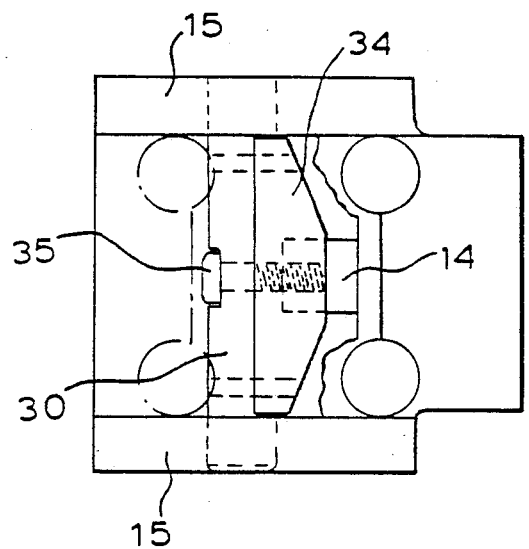
FIG. 4 is a section of the thigh link on the line X—X of FIG. 1.
Figures 7, 8:
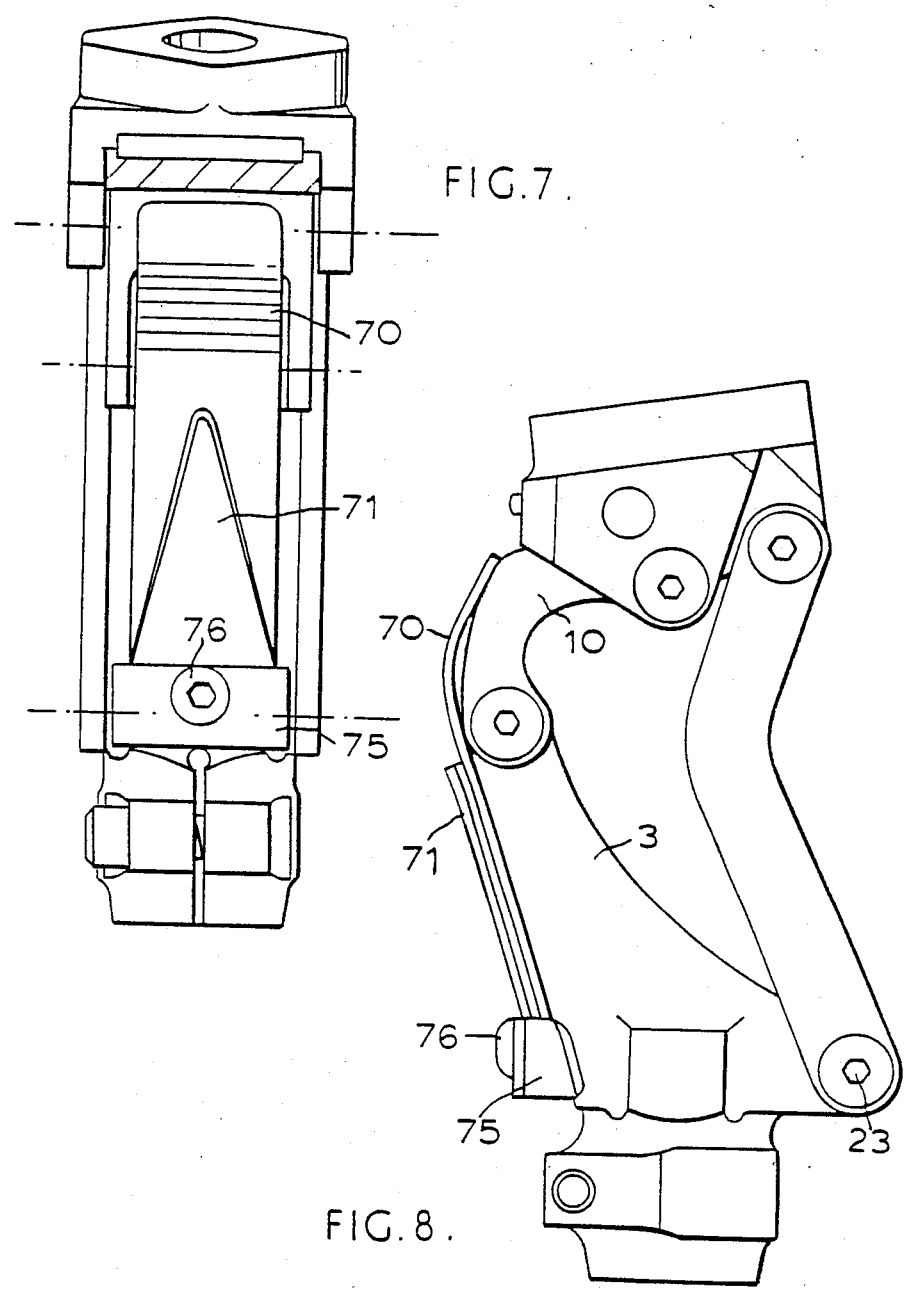
FIG. 7 is a front elevation of a knee mechanism according to the invention in the unflexed position and having a second form of an extension bias device fitted thereto.
FIGS. 8 and 9 are side elevations of the knee mechanism of FIG. 3 in the extended position and in a partly flexed position respectively.
Figure 9:
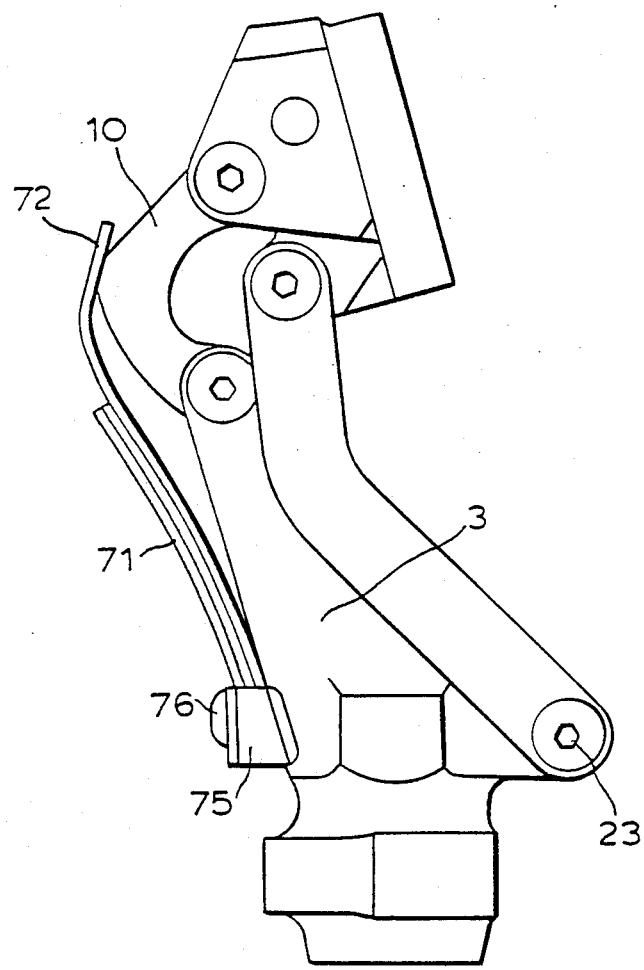

FIGS. 7, 8 and 9 show a second and preferred form of the extension bias mechanism where upstanding primary and secondary leaf springs 70, 71 are attached to the front face of the shin link 3 at approximately the same vertical position as the pivot 23. The primary leaf spring 70 has a posteriorly cranked tip 72 that bears against a front nose portion 74 (FIG. 2) of the anterior link 10. The movement of the link 10 is towards the posterior as the knee is unflexed and the spring 70 which is in compression biases the link 10 rearwardly, with the nose 74 sliding over the posterior face of spring 70. The secondary spring 71 is shorter than the primary spring 70 and is secured to lie over the lower part of the anterior face of spring 70 in the manner of a carriage spring. The springs 70, 71 are held to the link 3 by means of a block 75 and clamping screw 76.

We claim:

1. In a knee joint for an artificial leg rotatable between flexed and extended positions and comprising a four bar linkage consisting of thigh and shin link means pivotally connected to anterior and posterior link means to define a four bar linkage, the improvement comprising:

an extension buffer positioned to engage between the link means in a fully extended position of the joint, said buffer having a first portion of relatively soft material that serves to absorb kinetic energy as the joint is unflexed and a second portion of relatively hard material for reacting loads.

2. In a knee joint for an artificial leg rotatable between flexed and extended positions and comprising a four bar linkage consisting of thigh and shin link means pivotally connected to anterior and posterior link means to define a four bar linkage, the improvement comprising:

a leaf spring attached to the front of the shin link means and upstanding therefrom to bear against the anterior link means to bias the joint towards its extended position at low angles of flexion and to bias the joint towards its flexed position at high angles of flexion.

3. In a knee joint for an artificial leg rotatable between flexed and extended positions and comprising a four bar linkage consisting of thigh and shin link means pivotally connected to anterior and posterior link means to define a four bar linkage, the improvement comprising:

a leaf spring attached to the front of the shin link means and upstanding therefrom to bear against the anterior link means to bias the joint towards its extended position at low angles of flexion and to bias the joint towards its flexed position at high angles of flexion, said leaf spring means having a tip end cranked in a posterior direction.

4. In a knee joint for an artificial leg rotatable between flexed and extended positions and comprising a four bar linkage consisting of thigh and shin link means pivotally connected to anterior and posterior link means to define a four bar linkage, the improvement comprising:

a leaf spring attached to the front of the shin link means and upstanding therefrom to bear against the anterior link means to bias the joint towards its extended position at low angles of flexion and to bias the joint towards its flexed position at high angles of flexion, said leaf spring comprising a relatively long leaf attached directly to the shin link and a relatively short leaf attached to the shin link so as to overlie a lower portion of the outer face of the relatively long leaf.

5. In a knee joint for an artificial leg rotatable between flexed and extended positions and comprising a four bar linkage consisting of thigh and shin link means pivotally connected to anterior and posterior link means to define a four bar linkage, in which the anterior link means is cranked so that its thigh end is disposed rearwardly of central portions thereof and has upstanding catch means on a top face thereof, the anterior link means being pivotally connected to the thigh link means, posterior facing catch blade means pivotally supported on the thigh link means and resiliently biased to rotate downwardly, the arrangement being such that the blade travels over and is rotated by the catch means against the resistance of a return spring until the extended position is reached, when it snap engages an anterior face of the catch means; and a leaf spring attached to the front of the shin link means and upstanding therefrom to bear against the anterior link means to bias the joint towards its extended position at low angles of flexion and to bias the joint towards its flexed position at high angles of flexion.

6. A four bar knee mechanism for an artificial leg comprising thigh link means for attachment to upper portions of the leg, shin link means for attachment to a shin of the leg, and anterior and posterior link means pivoted between the thigh and shin link means, which:

(a) the line joining the pivot between the anterior link means and the shin link means to the pivot between the posterior link means and the shin link means sloping rearwardly and downwardly;

(b) the anterior link means being shorter than the posterior link means;

(c) the pivots on the shin link means spaced apart by more than twice the distance separating the pivots on the thigh link means;

(d) the pivots on the thigh link means disposed at intermediate positions relative to the horizontal positions of the pivots on the shin link means when the leg is in a fully extended position;

(e) the articulation defined by said links having an instantaneous center of rotation constituted by the intersection point of a line drawn through the pivots of the anterior link means and a line drawn through the pivots of the posterior link means, said center of rotation being located in substantially the region of that of a natural knee and lying upon a curve that is ascending through approximately 15° of flexion of the knee mechanism from its fully extended position;

(f) the posterior link means being of length and having a shin pivot position such that the articulation exhibits flexure exceeding 140° to enable both a natural sitting posture and a posture in which the user squats back on his heels.; and (g) spring means engaged between the shin link means and the anterior link means for biasing the joint toward its extended position at low angles of flexion and for biasing the joint toward its flexed position at high angles of flexion, said spring comprising a leaf spring attached to the front of the shin link and upstanding therefrom bears against the anterior link means.

7. An artificial leg according to claim 6, in which:

(a) the anterior and posterior link means are curved so that end portions thereof are disposed rearwardly of central portions thereof; and (b) the pivots are so disposed that when the mechanism is unflexed they define an irregular quadrilateral whose included angles are 157° at the thigh pivot of the anterior link means, 86° at the shin pivot of the anterior link means, 80° at the thigh pivot of the posterior link means and 37° at the shin pivot of the posterior link means; and (c) when the knee is unflexed, the line joining the thigh and shin pivots of the anterior link is directed downwardly at an angle of 49° to the vertical.

8. A four bar knee mechanism as claimed in claim 6, wherein:

said leaf spring has a tip end cranked in a posterior direction.

9. A four bar knee mechanism as claimed in claim 6, wherein:

the leaf spring comprises a relatively long leaf attached directly to the shin link and a relatively short leaf attached to the shin link so as to overlie a lower portion of the outer face of the relatively long leaf.

10. A four bar knee mechanism as claimed in claim 6, wherein:

the anterior link means is cranked so that its thigh end is disposed rearwardly of central portions thereof and has upstanding catch means on a top face, the anterior link means being pivotally connected to the thigh link means, posterior facing catch blade means pivotally supported on the thigh link means and resiliently biased to rotate downwardly, the arrangement being such that the blade travels over and is rotated by the catch means against the resistance of a return spring until the extended position is reached, when it snap engages an anterior face of the catch means.

11. A four bar knee mechanism for an artificial leg comprising thigh link means for attachment to upper portions of the leg, shin link means for attachment to a shin of the leg, and anterior and posterior link means pivoted between the thigh and shin link means, with:

(a) the line joining the pivot between the anterior link means and the shin link means to the pivot between the posterior link means and the shin link means sloping rearwardly and downwardly;

(b) the anterior link means being shorter than the posterior link means;

(c) the pivots on the shin link means spaced apart by more than twice the distance separating the pivots on the thigh link means;

(d) the pivots on the thigh link means disposed at intermediate positions relative to the horizontal positions of the pivots on the shin link means when the leg is in a fully extended position;

(e) the articulation defined by said links having an instantaneous center of rotation constituted by the intersection point of a line drawn through the pivots of the anterior link means and a line drawn through the pivots of the posterior link means, said center of rotation being located in substantially the region of that of a natural knee and lying upon a curve that is ascending through approximately 15° of flexion of the knee mechanism from its fully extended position;

(f) the posterior link means being of length and having a shin pivot position such that the articulation exhibits flexure exceeding 140° to enable both a natural sitting posture and a posture in which the user squats back on his heels;

(g) spring means engaged between the shin link means and the anterior link means for biasing the joint toward its extended position at low angles of flexion and for biasing the joint toward its flexed position at high angles of flexion; and (h) an extension buffer positioned to be engaged between the anterior link means and the thigh link means upon full extension of the joint, said buffer formed with a first portion of relatively soft material that serves to absorb kinetic enregy as the joint is unflexed and a second portion of relatively hard material for reacting loads.

12. A mechanism as claimed in claim 11, wherein a coil spring on a support coaxial with a pivot between the anterior link means and the shin link means has hooked limbs respectively engaging the anterior link means and the shin link means.

13. A knee joint for an artificial leg rotatable between flexed and extended positions and comprising a four bar linkage consisting of thigh and shin link means pivotally connected to anterior and posterior link means to define a four bar linkage, in which the anterior link means is cranked so that its thigh end is disposed rearwardly of central portions thereof and has upstanding catch means on its top face, the anterior link means being pivotally connected to the thigh link means, posterior facing catch blade means pivotally supported on the thigh link means and resiliently biased to rotate downwardly, the arrangement being such that the blade travels over and is rotated by the catch means against the resistance of a return spring until the extended position is reached, when it snap engages an anterior face of the catch means, said thigh link means having depending brackets, the catch blade means being supported on a carrier pivoted between the brackets of the thigh link means, and means provides for the blade to be extended from and returned towards the carrier.

* * * * *